(12) United States Patent
Bubon et al.

(10) Patent No.: US 12,262,463 B2
(45) Date of Patent: Mar. 25, 2025

(54) LIQUID COOLING SYSTEM FOR PRECISE TEMPERATURE CONTROL OF RADIATION DETECTOR FOR POSITRON EMISSION MAMMOGRAPHY

(71) Applicant: Radialis Medical, Inc., Thunder Bay (CA)

(72) Inventors: Oleksandr Bubon, Thunder Bay (CA); Alla Reznik, Thunder Bay (CA); Christopher Gillespie, Thunder Bay (CA)

(73) Assignee: Radialis Medical, Inc., Thunder Bay (CA)

( * ) Notice: Subject to any disclaimer, the term of this patent is extended or adjusted under 35 U.S.C. 154(b) by 0 days.

(21) Appl. No.: 17/270,611

(22) PCT Filed: Aug. 23, 2019

(86) PCT No.: PCT/CA2019/051164
§ 371 (c)(1),
(2) Date: Feb. 23, 2021

(87) PCT Pub. No.: WO2020/037430
PCT Pub. Date: Feb. 27, 2020

(65) Prior Publication Data
US 2021/0337650 A1    Oct. 28, 2021

Related U.S. Application Data

(60) Provisional application No. 62/722,490, filed on Aug. 24, 2018.

(51) Int. Cl.
*H05K 7/20*    (2006.01)
*A61B 6/00*    (2006.01)
(Continued)

(52) U.S. Cl.
CPC ........ *H05K 1/0203* (2013.01); *A61B 6/4488* (2013.01); *G01T 1/2985* (2013.01);
(Continued)

(58) Field of Classification Search
CPC ............ H05K 1/0203; H05K 7/20254; H05K 7/20281; H05K 2201/10151; A61B 6/4488; A61B 6/037; A61B 6/502; G01T 1/2985
(Continued)

(56) References Cited

U.S. PATENT DOCUMENTS 6,104,003 A * 8/2000 Jones ............... H05K 7/207
219/400
8,668,560 B2 * 3/2014 Zuzek ............... B67D 7/84
454/228
(Continued)

FOREIGN PATENT DOCUMENTS

CN   1475192 A   2/2004
CN   102283668 A   12/2011
(Continued)

OTHER PUBLICATIONS

JP-2008267623-A-English translation (Year: 2008).*
(Continued)

*Primary Examiner* — Anatoly Vortman
(74) *Attorney, Agent, or Firm* — Quarles & Brady LLP

(57) ABSTRACT

A temperature control assembly that enables precise temperature control for radiation detectors, such as positron emission tomography ("PET") detectors and other densely packed electronics is described. The temperature control assembly includes a liquid cooling assembly that generally includes a cold plate having formed therein one or more channels through which a liquid coolant is able to flow. The channels are enclosed by the cold plate, such that the liquid
(Continued)

coolant does not come into contact with sensitive electronic components used in the radiation detectors. When a liquid coolant is flowing through the channels, a sufficiently low humidity level is maintained external the cold plate. The liquid cooling assembly is removable and can be arranged between layers of printed circuit boards in an array of radiation detectors. Heating elements can be coupled the liquid cooling assembly and operated to increase the temperature as necessary to maintain a precisely controlled temperature environment.

15 Claims, 6 Drawing Sheets

(51) Int. Cl.
*G01T 1/29* (2006.01)
*H05K 1/02* (2006.01)
*A61B 6/03* (2006.01)
*A61B 6/50* (2024.01)

(52) U.S. Cl.
CPC .......... *H05K 7/20254* (2013.01); *A61B 6/037* (2013.01); *A61B 6/502* (2013.01); *H05K 2201/10151* (2013.01)

(58) Field of Classification Search
USPC ........................................................ 361/699
See application file for complete search history.

(56) References Cited

U.S. PATENT DOCUMENTS

| | | | | |
|---|---|---|---|---|
| 8,938,880 | B2* | 1/2015 | Loong | H01L 23/473 |
| | | | | 29/890.03 |
| 10,001,569 | B2* | 6/2018 | McBroom | G01T 1/2985 |
| 2003/0047685 | A1 | 3/2003 | Sobel et al. | |
| 2004/0035847 | A1 | 2/2004 | Gat | |
| 2005/0100128 | A1 | 5/2005 | Hilderscheid et al. | |
| 2006/0278372 | A1* | 12/2006 | Lai | H01L 23/467 |
| | | | | 165/80.4 |
| 2010/0085124 | A1* | 4/2010 | Stolpman | H03L 1/04 |
| | | | | 331/70 |
| 2012/0175094 | A1* | 7/2012 | Rice | F28F 3/12 |
| | | | | 165/170 |
| 2013/0037251 | A1* | 2/2013 | Joshi | G05D 23/1919 |
| | | | | 378/19 |
| 2013/0284936 | A1* | 10/2013 | McBroom | G01R 33/481 |
| | | | | 250/363.03 |
| 2016/0011060 | A1* | 1/2016 | Bergen | H02N 13/00 |
| | | | | 374/161 |
| 2016/0081178 | A1* | 3/2016 | D'Onofrio | H05K 7/20218 |
| | | | | 361/699 |
| 2017/0059720 | A1* | 3/2017 | McBroom | G01T 1/2985 |
| 2018/0035957 | A1 | 2/2018 | Liu et al. | |

FOREIGN PATENT DOCUMENTS

| | | | |
|---|---|---|---|
| JP | 2008267623 A | * | 11/2008 |
| JP | 2009194021 A | | 8/2009 |
| JP | 5082610 B2 | * | 11/2012 |

OTHER PUBLICATIONS

JP-5082610-B2-English translation (Year: 2012).*
Dohle, Rainer, et al. "LTCC-based highly integrated SiPM module with integrated liquid cooling channels for high resolution molecular imaging." Journal of Microelectronics and Electronic Packaging 15.2 (2018): 86-94.
Second Office Action in Chinese Application No. 201980069553.3; received on Nov. 28, 2024.

* cited by examiner

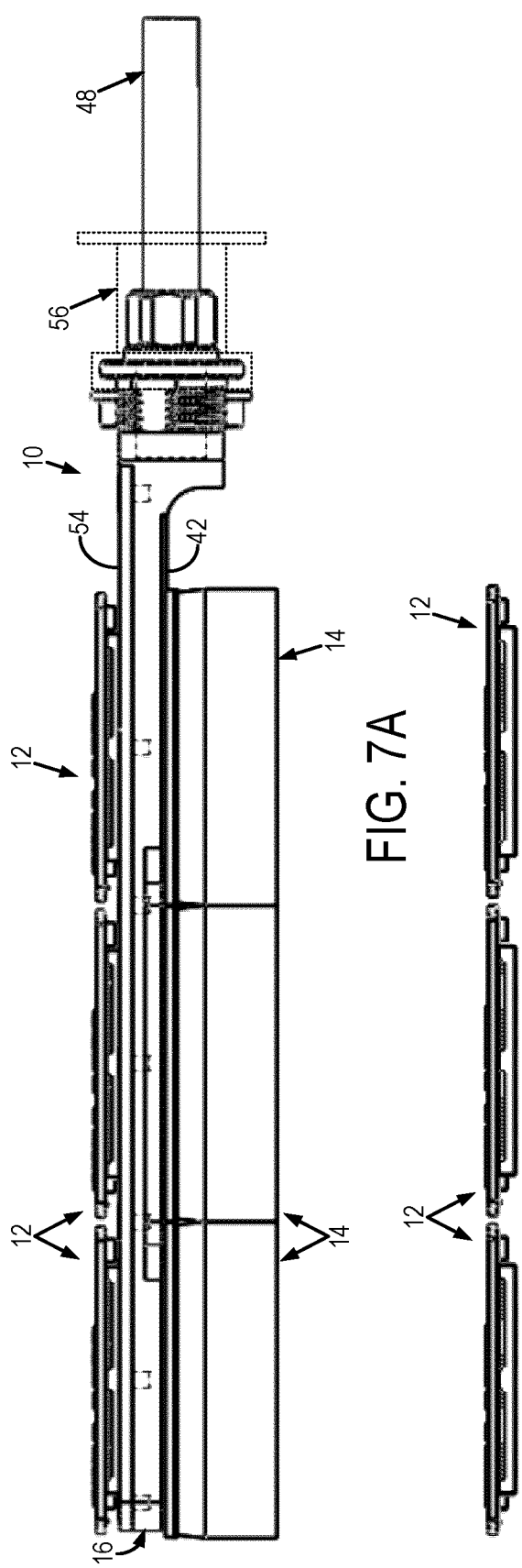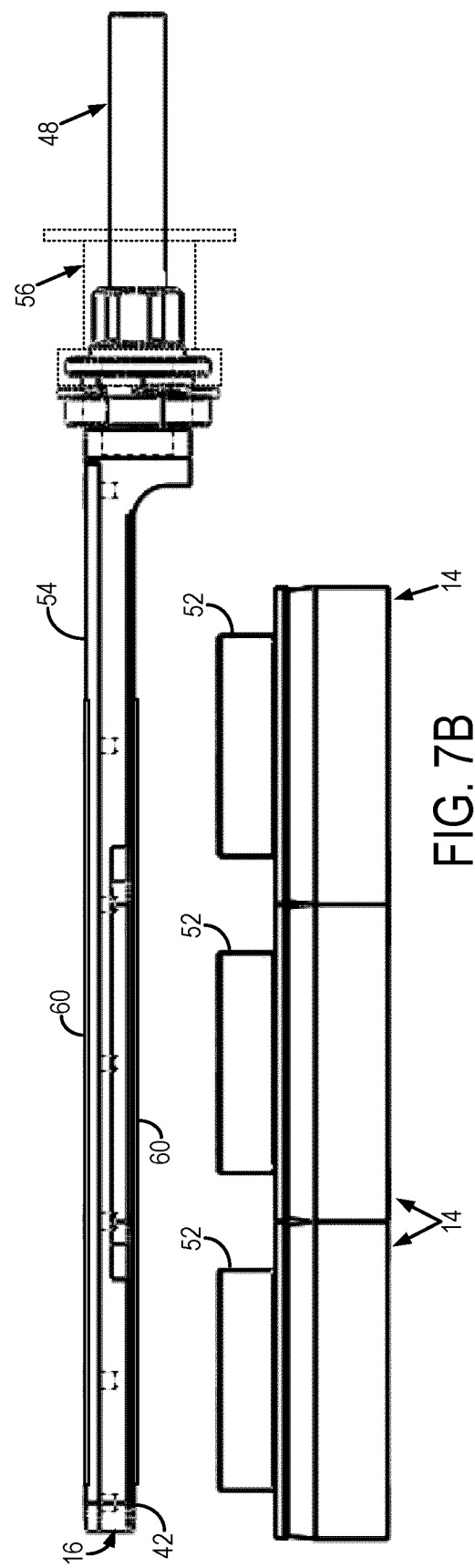

LIQUID COOLING SYSTEM FOR PRECISE TEMPERATURE CONTROL OF RADIATION DETECTOR FOR POSITRON EMISSION MAMMOGRAPHY

CROSS-REFERENCE STATEMENT

This application is the U.S. national stage entry of international application PCT/CA2019/051164, filed Aug. 23, 2019, which claims the benefit of U.S. Provisional Patent Application Ser. No. 62/722,490, filed on Aug. 24, 2018, the contents of which are incorporated herein by reference in their entireties.

BACKGROUND

Radiation detectors can generate a significant amount of heat that needs to be properly dissipated. Most radiation detectors use air to cool the electrical components of the detector, such as the signal amplification and processing circuits. Additionally, operation properties of solid-state sensors, used in radiation detectors, are highly dependent on temperature and humidity. Small changes in temperature during operation may result in significant change in gain, noise, and timing properties of the whole system. Thus, a need exists to be able to precisely control the temperature of solid-state sensors and the environment around such sensors, while at the same time efficiently cooling down active components of the signal electronics that are typically located in close proximity to the sensor. While there is a desire to construct densely packed radiation detectors, such as tiled arrays of radiation detectors, for positron emission mammography and other imaging modalities, these more compact radiation detectors have an increased heat density that must be properly addressed.

There is a desire, then, to provide a precise temperature control system that is capable of removing heat from a densely packed array of radiation detectors, while maintaining stable temperature for sensor operation.

SUMMARY OF THE DISCLOSURE

The present disclosure addresses the aforementioned drawbacks by providing a temperature control assembly that includes a cold plate, a channel formed in the cold plate, an inlet formed in the channel, an outlet formed in the channel, and at least one aperture formed in the cold plate. The cold plate has a first contact surface and a second contact surface opposite the first contact surface, and is composed of a thermally conductive material. The channel formed in the cold plate is enclosed by the cold plate between the first contact surface and the second contact surface of the cold plate. The inlet formed in the channel provides inflow of a liquid to the channel, and the outlet formed in the channel provides for outflow of the liquid from the channel. The at least one aperture formed in the cold plate is sized to receive an electrical connection between a printed circuit board when the printed circuit board is coupled to the first contact surface of the cold plate and a photodetector assembly when the photodetector assembly is coupled to the second contact surface of the cold plate.

It is another aspect of the present disclosure to provide a liquid-cooled radiation detector that includes a first printed circuit board having arranged thereon at least one preamplifier, a second printed circuit board electrically connected to a photodetector, and a removable liquid cooling assembly arranged between the first and second printed circuit board. The removable liquid cooling assembly includes a cold plate composed of a thermally conductive material and a channel formed in and enclosed by the cold plate. The channel is formed such that a liquid coolant flowing through the channel removes heat transferred to the cold plate from the first printed circuit board and the second printed circuit board while maintaining a sufficiently low level of humidity external the cold plate such that the first printed circuit board and the second printed circuit board are not damaged by humidity when the liquid coolant is flowing through the channel.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 7A shows a side view of an example tiled radiation detector array using a liquid cooling assembly in accordance with some embodiments described in the present disclosure.

FIG. 7B shows an exploded side view of the example tiled radiation detector array shown in FIG. 7A.

DETAILED DESCRIPTION

Described here are systems and methods for temperature controlled radiation detectors, such as liquid-cooled positron emission tomography ("PET") detectors. Particularly, temperature control is provided by a temperature control assembly that may include a liquid cooling assembly having a cold plate having formed therein one or more channels through which a liquid coolant is able to flow. The one or more channels are enclosed by the cold plate, such that the liquid coolant does not come into contact with sensitive electronic components used in the radiation detectors. In some embodiments, heating elements are provided to the cold plate of the liquid cooling assembly, which can be controlled to provide an additional level of temperature control. The precision of temperature control provided by the heating elements enables the maintenance of temperature for optimal performance of the radiation detector and associated electronics.

Figure 1:
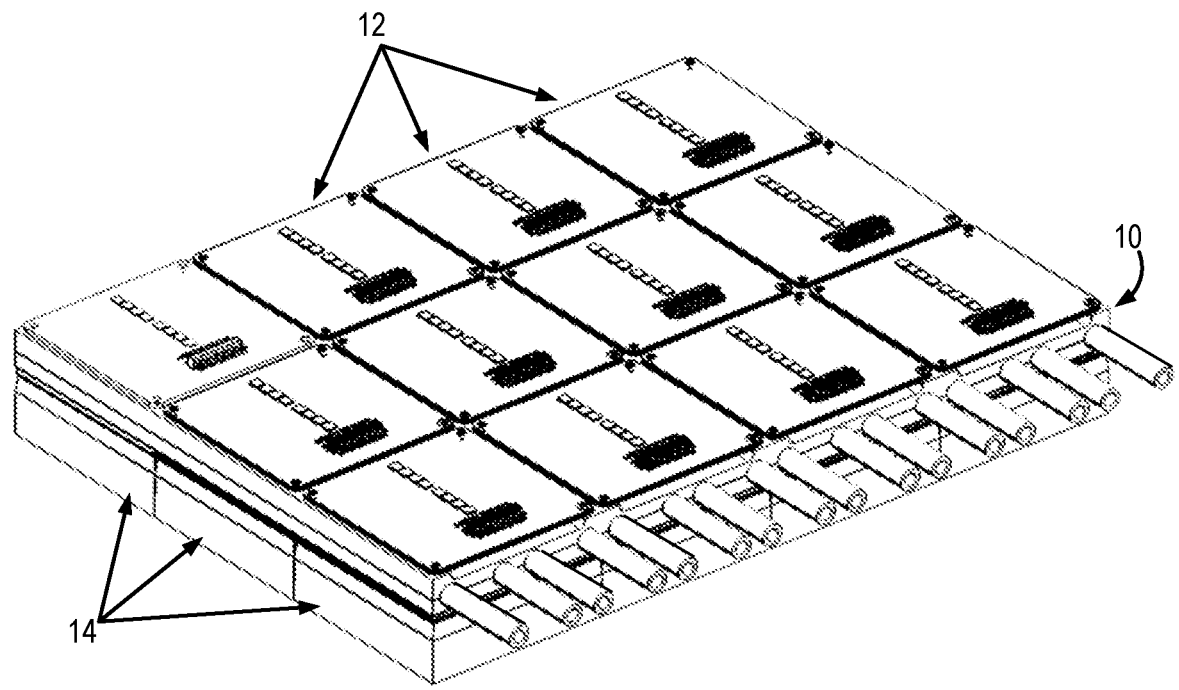
FIG. 1 shows an example of a liquid cooling assembly, in accordance with some embodiments described in the present disclosure, arranged between an array of printed circuit boards ("PCBs") and photodetector assemblies that collectively form a tiled array of radiation detectors.
Figure 2:
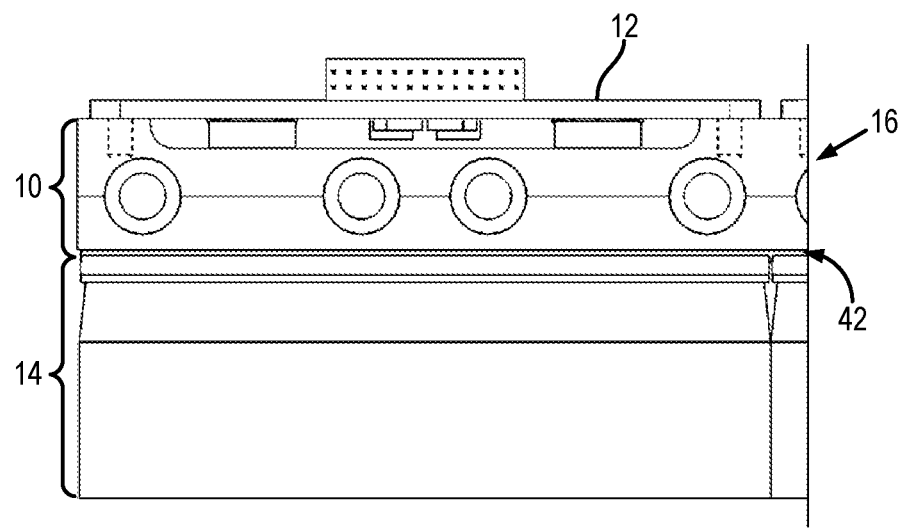
FIG. 2 shows a cross section through the tiled array of radiation detectors shown in FIG. 1.

As shown in FIGS. 1 and 2, the temperature control, which may include liquid cooling, is provided by a liquid cooling assembly 10 that is designed to be removably positioned between a printed circuit board ("PCB") 12 and a photodetector assembly 14 of a tileable block detector. An example of tileable block detectors is described in co-pending PCT Application No. PCT/CA2017/050228, which is herein incorporated by reference in its entirety.

Figure 3:
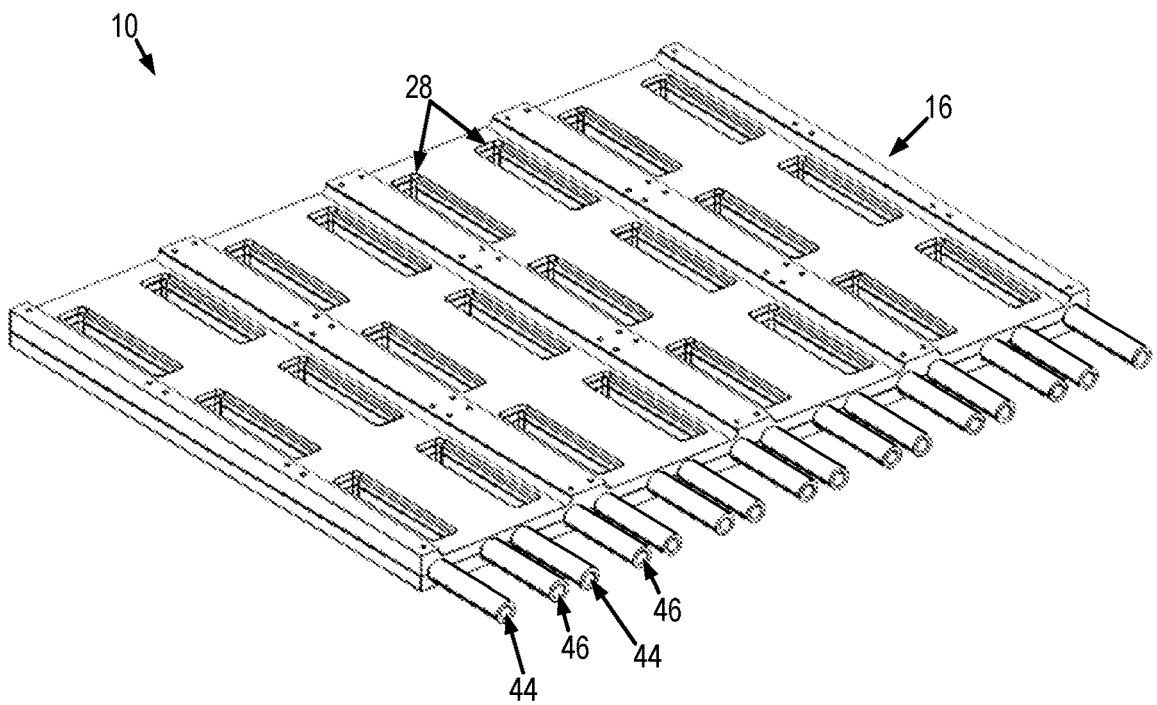
FIG. 3 shows an example of a liquid cooling assembly in accordance with some embodiments described in the present disclosure.
Figure 4A:
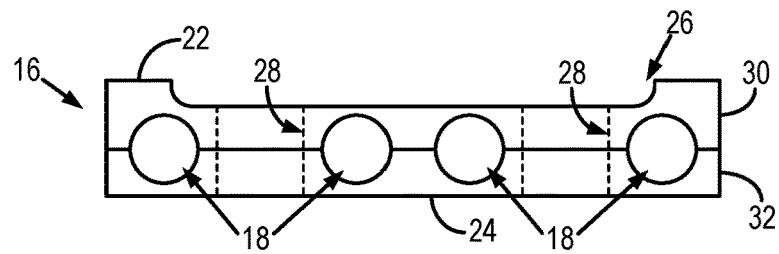
FIG. 4A shows a cross sectional view of an embodiment of a liquid cooling assembly as described in the present disclosure.
Figure 4B:
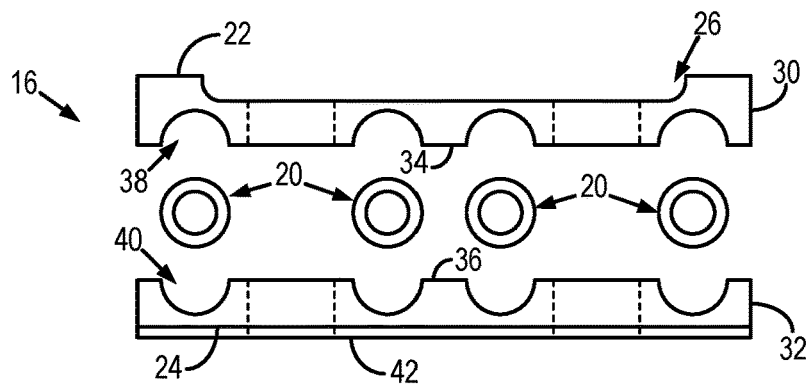
FIG. 4B shows an exploded cross sectional view of another embodiment of a liquid cooling assembly described in the present disclosure.

As shown in FIGS. 3, 4A, and 4B, the liquid cooling assembly 10 generally includes a cold plate 16 having formed therein one or more channels 18 into which one or more tubes 20 are arranged. A liquid is provided to circulate through the one or more tubes 20 or channels 18 to remove heat that is transferred to the cold plate 16 from components on the PCB 12, the photodetector assembly 14, or both. In some embodiments, no tubes 20 are arranged in the channels 18, and instead the liquid is provided directly to the channels 18. FIG. 4A shows a cross section of an example cold plate 16 in which no tubes 20 are arranged in the channels 18, and FIG. 4B shows an exploded cross section of an example cold plate 16 in which tubes 20 are arranged in the channels 18.

The cold plate 16 has a first contact surface 22 that is placed into contact with the PCB 12, and a second contact surface 24 that is opposite the first contact surface 22 and which is placed into contact with the photodetector assembly 14. In some embodiments, the first contact surface 22 may directly contact the PCB 12, but in some other embodiments one or more layers (e.g., insulating or conductive layers) may be provided between the first contact surface 22 and the PCB 12.

A recess 26 is formed on the first contact surface 22 side of the cold plate 16, such that components on the PCB 12 are allowed to extend into the recessed region 26 when the PCB 12 is coupled to the first contact surface 22 of the cold plate 16.

One or more apertures 28 are formed in the cold plate 16 extending from the second contact surface 24 through to the surface in the recessed region 26. The apertures 28 allow for electrical connectors to pass between the PCB 12 and the photodetector assembly 14. For instance, the photodetector assembly 14 can include a circuit board on which sensors or other data acquisition components are located, and electrical connectors can extend through the apertures 28 to electrically connect the sensor circuit boards with preamp circuit components located on the PCB 12. This construction allows the overall thickness of the cold plate 16 to be reduced. As one example, the thickness of the cold plate 16 can be up to 9.6 mm.

In some embodiments, the cold plate 16 includes an upper plate 30 and a lower plate 32 that is opposite the upper plate 30. As shown in FIG. 4B, the upper plate 30 includes an outward facing surface, which corresponds to the first contact surface 22 of the cold plate 16, and an inward facing surface 34 that is opposite the first contact surface 22. Likewise, the lower plate 32 includes an outward facing surface that corresponds to the second contact surface 24 of the cold plate 16, as well as an inward facing surface 36 that is opposite the second contact surface 24. In these instances, the inward facing surface 34 of the upper plate 30 has formed therein upper channel portions 38 and the inward facing surface 36 of the lower plate 32 has matching lower channel portions 40 formed therein. When the inward facing surface 34 of the upper plate 30 is brought into contact with the inward facing surface 36 of the lower plate 32, the upper channel portions 38 and the lower channel portions 40 meet to form the plurality of channels 18. As mentioned above, in some embodiments, one or more tubes 20 are arranged in the plurality of channels and thus can be disposed between the upper plate 30 and the lower plate 32.

As shown in FIG. 4B, in some embodiments, the outward facing surface of the lower plate 32, which corresponds to the second contact surface 24 of the cold plate 16, can have coupled thereto a thermally conductive pad 42 that can be composed of a compressible material, such that mismatches between the cold plate 16 and the faces of the PCB 12 and photodetector assembly 14 can be taken up, thereby increasing the contact surface of the cold plate 16. Preferably, the thermally conductive pad 42 is composed of a material that is electrically insulating (i.e., has a relatively high dielectric constant). As one non-limiting example, the electrically insulating material can be a silicone elastomer. As another non-limiting example, the electrically insulating material can be a polyimide. The thermally conductive pad 42 can be coupled to the second contact surface 24 using an adhesive, and may have formed therein apertures similar to the apertures 28 formed in the cold plate 16.

In some embodiments, one or more heating elements 60 can be coupled to the first contact surface 22, the second contact surface 24, or both. As one example, the heating elements 60 can be coupled to the second contact surface 24 via coupling to the thermally conductive pad 42. As an example, the one or more heating elements 60 can include a thin film heating pad. The thin film heating pad can be constructed as an etched foil, which may be embedded in a substrate material, such as silicon or Kapton wrap, to provide electrical insulation. The one or more heating elements 60 can be controlled via a controller in order to precisely control the temperature of the radiation detector assembly or its associated electrical components.

As an example, under high load of radiation, more heat will be generated by preamplifiers, therefore resulting in more powerful cooling. In these instances, the temperature of the sensors in the radiation detector assembly may change significantly, which is undesirable because such sensors are often highly sensitive to changes in temperature. The one or more heating elements 60 can then be operated to increase the temperature of the radiation detector assembly, or its associated electrical components, to avoid overcooling and to maintain the radiation detector assembly operating within a temperature range in which the sensors have optimal or otherwise satisfactory performance. In some embodiments, a temperature sensor can be provided and coupled to the liquid cooling assembly 10 in order to monitor temperature. Feedback from the temperature sensor can then be used to control the operation of the heating elements 60 to precisely adjust the temperature of the radiation detector assembly in those instances where the radiation detector assembly may be overcooled by the liquid cooling assembly. For instance, power to the heating elements 60 can be controlled such that the heating elements 60 start heating only when the temperature of the sensors in the radiation detector assembly is changing.

The upper plate 30 and the lower plate 32 can be composed of the same material, or in some instances can be composed of different materials. As one example, the upper plate 30 and the lower plate 32 can both be composed of copper or other thermally conductive metals, metal alloys, plastics, carbon fiber, carbon fiber epoxies, or other materials.

Figure 5:
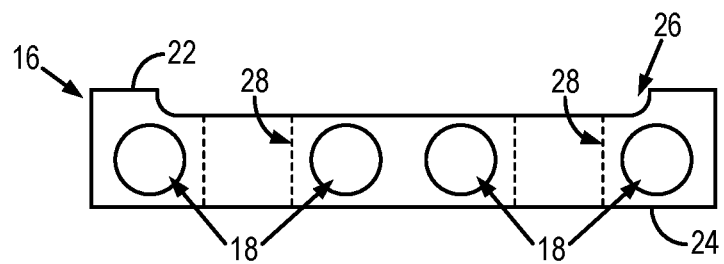
FIG. 5 shows a cross sectional view of another embodiment of a liquid cooling assembly as described in the present disclosure.

In some embodiments, the cold plate 16 includes a single piece in which the one or more channels 18 are machined or otherwise formed, as shown in FIG. 5. In these instances, the cold plate 16 has a first contact surface 22 that is placed into contact with the PCB 12, and a second contact surface 24 opposite the first contact surface 22, which is placed into contact with the photodetector assembly 14. A thermally conductive pad 42 may also be coupled to the second contact surface 24, as noted above.

The cold plate 16 can be dimensioned to provide thermal control (e.g., cooling, heating, or both) to a single tileable radiation detector, a large area monolithic radiation detector, or multiple tileable radiation detectors that are arranged in an array. For instance, the cold plate 16 can be dimensioned to provide cooling to an M×N array of tileable radiation detectors. In other instances, the cold plate 16 can be dimensioned to provide cooling to an M×1 or 1×N array of tileable radiation detectors. In these latter configurations, multiple cold plates 16 can be arrayed to provide cooling to larger array of tileable radiation detectors. These configurations have an advantage that if there is a failure in one of the cold plates 16 that particular cold pate 16 can be removed from the liquid cooling assembly 10 and replaced with a properly functioning cold plate 16 without having to replace the entire liquid cooling assembly.

As shown in FIG. 3, in some embodiments, each tube 20 has an inlet 44 and an outlet 46. In other embodiments, each channel 18 may have more than one inlet, more than one outlet, or combinations thereof. In those embodiments where a tube 20 is not arranged in the channel 18, then the inlet 44 and outlet 46 are formed in the channel 18 instead of the tube 20.

Figure 6:
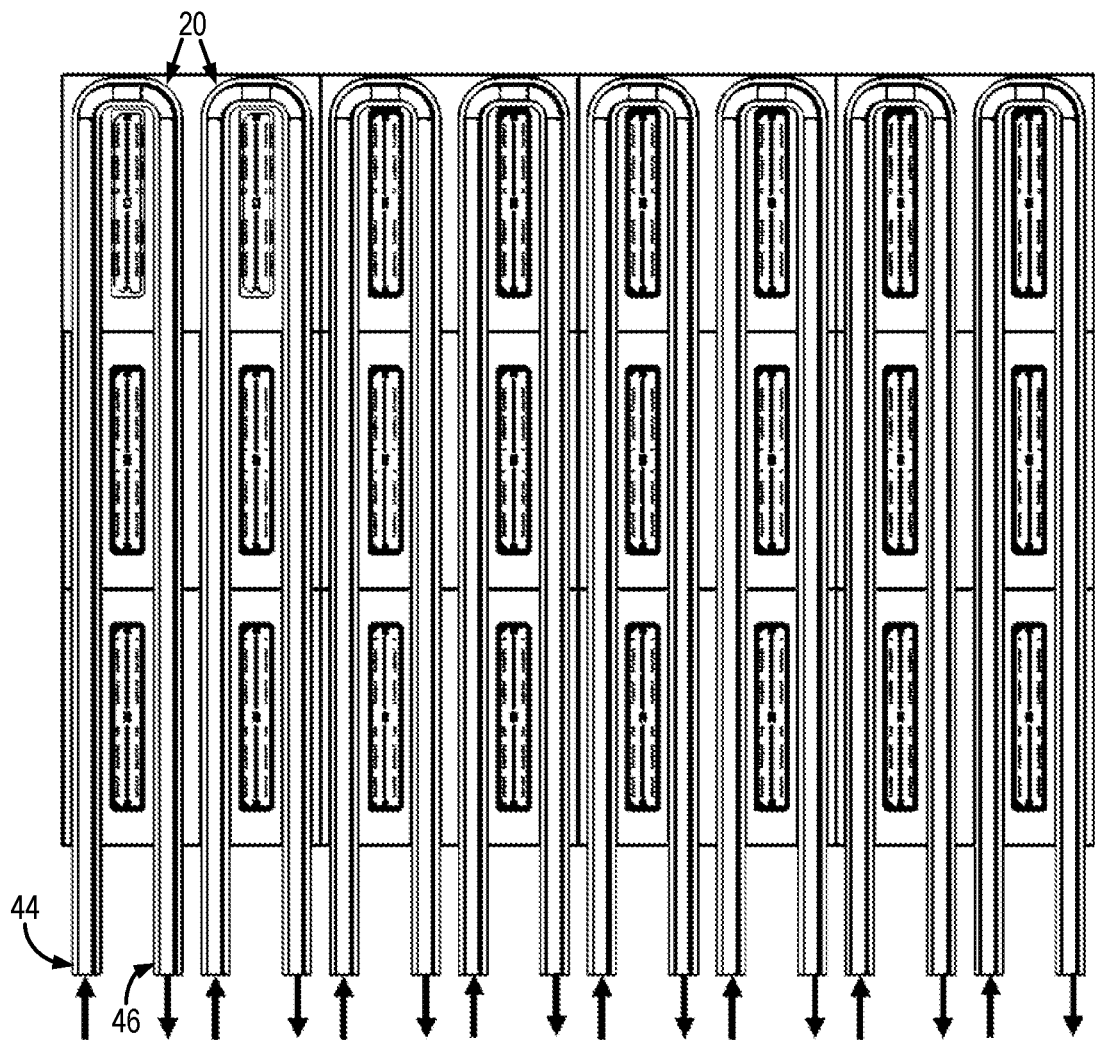
FIG. 6 shows a schematic representation of an example arrangement of tubes, and their inflow and outflow, for use in a liquid cooling assembly, relative to photodetector assemblies of tileable radiation detectors.

In some embodiments, the channels 18, tube 20, or both, are constructed to form separate loops to maximize temperature uniformity, as shown in FIG. 6. In such instances, each channel 18, tube 20, or both can be U-shaped, or can have other shapes and configurations. For ease of use, the inlet 44 and outlet 46 can be arranged on the same side of the cold plate 16, but in other configurations the inlet 44 and outlet 46 can be arranged on different sides of the cold plate 16.

A separate line can be provided to each inlet 44 to provide inflow of a liquid into the channels 18, and a separate line can be provided to each outlet 46 to provide outflow of the liquid from the channels 18. In some embodiments, a manifold can be provided to connect each inlet 44 together to a common inflow line and to connect each outlet 46 together to a common outflow line. The manifold can include a single structure that keeps the inlet 44 lines and outlet 46 lines separate, or can include two separate structures, one for the inlet 44 lines and one for the outlet 46 lines.

FIGS. 7A-7D show an example in which a liquid cooling assembly 10 is arranged between an array of PCBs 12 and photodetector assemblies 14 corresponding to an array of tileable radiation detectors. In this example, liquid coolant is provided to the liquid cooling assembly via an inflow line 48. As the liquid coolant passes through the tubes 20 in the liquid cooling assembly 10 it removes heat from the PCBs 12 and photodetector assemblies 14. The liquid coolant then leaves the liquid cooling assembly via an outflow line 50, after which the liquid coolant can be cooled again for later use, recycled, or otherwise stored.

Preferably, the inflow line 48 and the outflow line 50 are composed of a flexible material, such as a flexible PVC. In these instances, the radiation detector (e.g., a tileable block detector composed of PCBs 12 and photodetector assemblies 14) can be moved without needing to disconnect the cold plate 16. Such functionality is advantageous for medical procedures, such as those where it may be desired to perform a biopsy during which the radiation detector assembly needs to be moved to provide access to the patient. Such functionality can also be advantageous for multimodality imaging applications where it may be necessary to move the radiation detector assembly to provide access for other imaging modalities, such as x-ray or ultrasound imaging. As shown, light-tight flexible shrouds 56 can be coupled to the inflow line 48 and the outflow line 50 in order to enable flexible tubing connection while maintaining light tightness for detector operation. As one example, the light-tight flexible shrouds 56 can be composed of silicone.

As seen in FIG. 7B, the photodetector assemblies 14 include an electrical connector 52 that extends through the apertures 28 formed in the cold plate 16 in order to engage and electrically connect to the PCBs 12, as mentioned above.

In this example, the cold plate 16 does not have a recess 26 formed in the first contact surface 22 side. In some embodiments, it will be appreciated that the apertures 28 can be sized and arranged such that some or all of the components on the PCBs 12 facing the first contact surface 22 extend into the apertures 28 when the PCBs 12 are coupled to the cold plate 16.

Figure 7C:
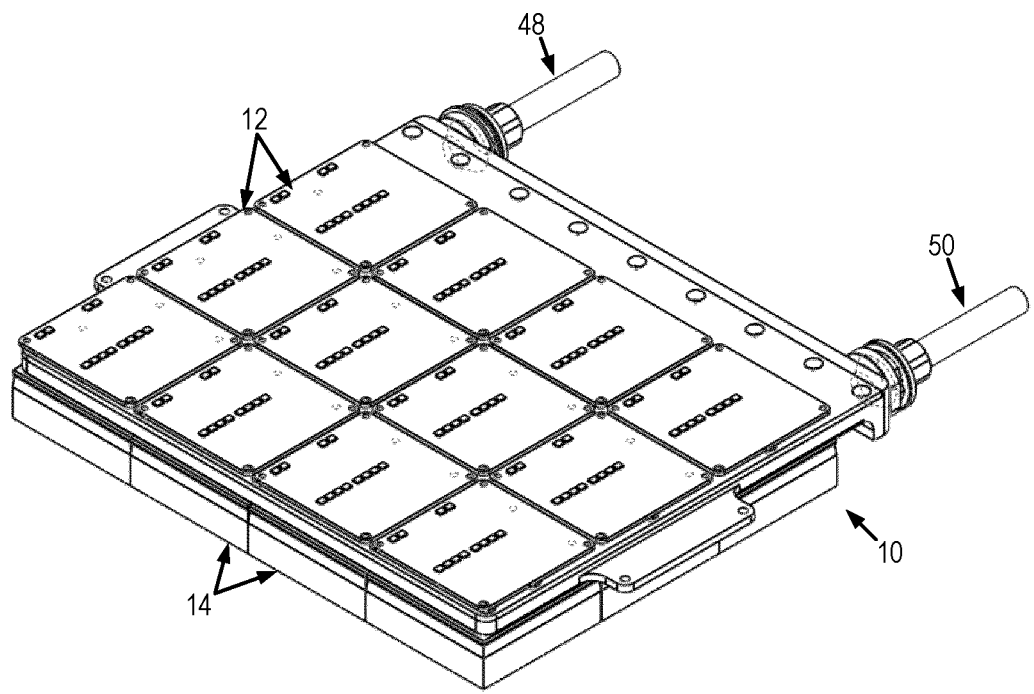
FIG. 7C shows another view of the example tiled radiation detector array show in FIG. 7A.
Figure 7D:
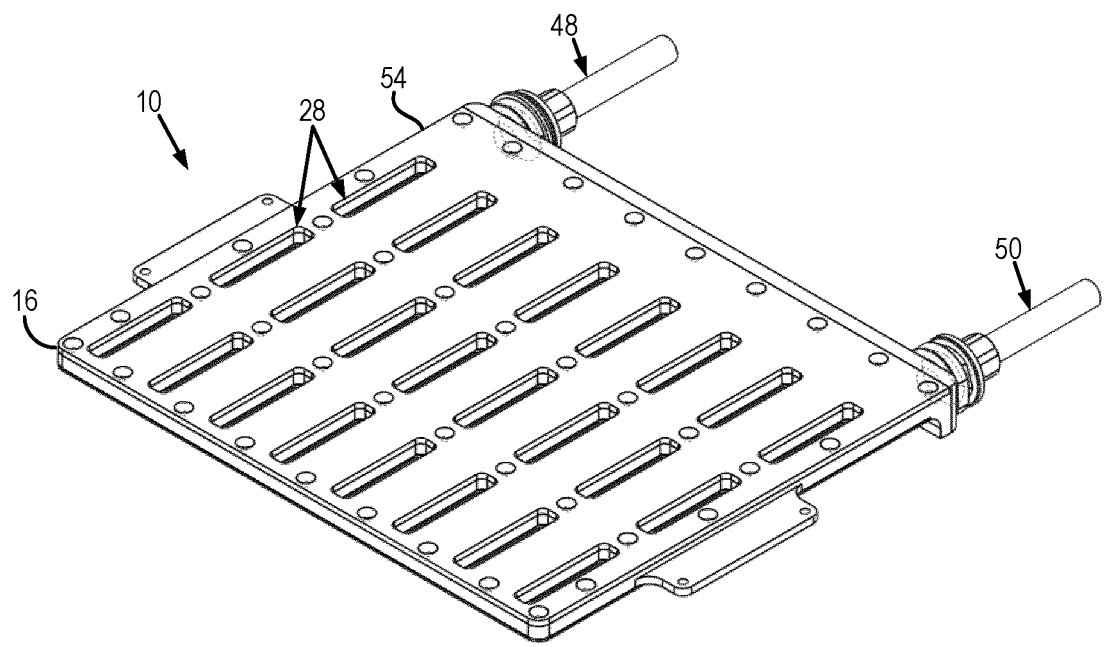
FIG. 7D shows a view of the liquid cooling assembly used in the example tiled radiation detector array shown in FIG. 7A.
Figure 8:
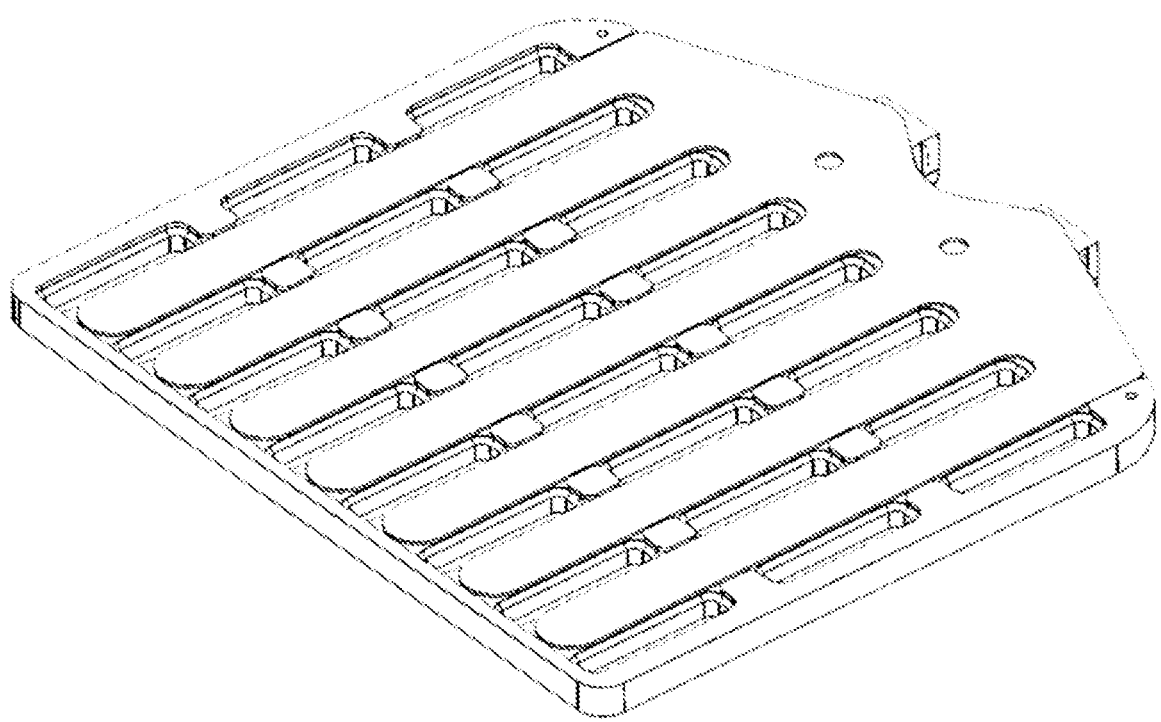
FIG. 8 shows another embodiment of a liquid cooling assembly described in the present disclosure.

As seen in FIGS. 7B and 7D, an electrically insulating layer 54 can be coupled to the first contact surface 22 of the cold plate 16. As one example, the electrically insulating later 54 can be composed of a continuous-woven glass fabric laminate with an epoxy resin, such as FR4 Garolite® (McMaster-Carr), or other epoxy sheets or plastic sheets or laminates or carbon fiber compositions. The electrically insulating layer 54 can also reduce the thermal conductivity FIG. 8 illustrates another example of a liquid cooling assembly 10 in which the cold plate 16 is composed of a bonded aluminum assembly, lid, and main body. The cold plate 16 has an anodized finish, with contact face machined to expose metal. A compressible thermal pad can be coupled to the contact face. The liquid cooling assembly 10 shown in FIG. 8 is sized to fit between a preamp PCBs and a sensor PCBs of photodetector assemblies. The liquid cooling assembly 10 shown in FIG. 8 provides single path cooling with one port in and one port out.

The present disclosure has described one or more preferred embodiments, and it should be appreciated that many equivalents, alternatives, variations, and modifications, aside from those expressly stated, are possible and within the scope of the invention.

The invention claimed is:

1. A temperature control assembly, comprising:
   a cold plate having a first contact surface and a second contact surface opposite the first contact surface, wherein the cold plate is composed of a thermally conductive material;
   a channel formed in the cold plate and enclosed by the cold plate between the first contact surface and the second contact surface of the cold plate;
   an inlet formed in the channel for providing inflow of a liquid to the channel;
   an outlet formed in the channel for providing outflow of the liquid from the channel;

at least one aperture formed in the cold plate, wherein the aperture receives an electrical connection between a printed circuit board when the printed circuit board is coupled to the first contact surface of the cold plate and a photodetector assembly when the photodetector assembly is coupled to the second contact surface of the cold plate;

a thermally conductive pad coupled to the second contact surface;

a heating element coupled to the thermally conductive pad; and a temperature sensor that measures a temperature of electrical components mounted to the printed circuit board when the printed circuit board is coupled to one of the first contact surface or the second contact surface, and wherein the temperature sensor provides the measured temperature to a controller in order to control a power supplied to the heating element.

2. The temperature control assembly as recited in claim 1, further comprising a recess formed in the first contact surface of the cold plate to receive electrical components mounted to the printed circuit board when the printed circuit board is coupled to the first contact surface of the cold plate.

3. The temperature control assembly as recited in claim 1, further comprising a tube arranged in the channel, wherein the tube is composed of a thermally conductive material.

4. The temperature control assembly as recited in claim 1, wherein the cold plate comprises an upper plate in contact with a lower plate, the upper plate having an outward facing surface corresponding to the first contact surface and an inward facing surface opposite the outward facing surface, and the lower plate having an outward facing surface corresponding to the second contact surface and an inward facing surface opposite the outward facing surface, wherein the inward facing surface of the upper plate is in contact with the inward facing surface of the lower plate.

5. The temperature control assembly as recited in claim 4, wherein an upper channel portion is formed in the inward facing surface of the upper plate and a lower channel portion is formed in the inward facing surface of the lower plate, such that when the inward facing surface of the upper plate is in contact with the inward facing surface of the lower plate then upper channel portion and the lower channel portion form the channel.

6. The temperature control assembly as recited in claim 4, wherein the upper plate is composed of a first thermally conductive material and the lower plate is composed of a second thermally conductive material that is different from the first thermally conductive material.

7. The temperature control assembly as recited in claim 1, wherein the cold plate is composed of copper.

8. The temperature control assembly as recited in claim 1, wherein the thermally conductive pad is composed of a compressible material.

9. The temperature control assembly as recited in claim 1, wherein the heating element comprises a thin film heating element.

10. The temperature control assembly as recited in claim 9, wherein the thin film comprises an etched foil.

11. The temperature control assembly as recited in claim 1, wherein the heating element is coupled to the thermally conductive pad via a layer of thermally conductive material.

12. The temperature control assembly as recited in claim 1, further comprising an electrically insulating layer arranged on the first contact surface.

13. The temperature control assembly as recited in claim 12, wherein the electrically insulating layer is composed of an FR4 glass epoxy laminate.

14. The temperature control assembly as recited in claim 1, wherein the channel comprises a plurality of channels, and each of the plurality of channel has a corresponding inlet and outlet formed therein.

15. The temperature control assembly as recited in claim 14, wherein a tube is arranged in each of the plurality of channel, and wherein each tube is composed of a thermally conductive material.

\* \* \* \* \*